US010488065B2

(12) United States Patent
Chen et al.

(10) Patent No.: US 10,488,065 B2
(45) Date of Patent: Nov. 26, 2019

(54) LEAK DETECTION UNIT FOR REFRIGERANT SYSTEM

(71) Applicant: Carrier Corporation, Farmington, CT (US)

(72) Inventors: Lei Chen, South Windsor, CT (US); Zhiwei Yang, South Windsor, CT (US); Warren Clough, Cicero, NY (US); Larry D. Burns, Avon, IN (US); Ivan Rydkin, Rochester, NY (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 747 days.

(21) Appl. No.: 14/962,461

(22) Filed: Dec. 8, 2015

(65) Prior Publication Data
US 2016/0178229 A1    Jun. 23, 2016

Related U.S. Application Data

(60) Provisional application No. 62/093,152, filed on Dec. 17, 2014.

(51) Int. Cl.
| | |
|---|---|
| *G01N 27/407* | (2006.01) |
| *F24F 11/36* | (2018.01) |
| *G01M 3/22* | (2006.01) |
| *F24F 11/30* | (2018.01) |
| *F24F 11/70* | (2018.01) |
| *G01N 27/30* | (2006.01) |
| *G01M 3/20* | (2006.01) |
| *G01N 27/404* | (2006.01) |
| *F24F 110/50* | (2018.01) |
| *F24F 110/66* | (2018.01) |

(52) U.S. Cl.
CPC .............. *F24F 11/36* (2018.01); *F24F 11/30* (2018.01); *F24F 11/70* (2018.01); *G01M 3/228* (2013.01); *G01N 27/4075* (2013.01); *F24F 2110/50* (2018.01); *F24F 2110/66* (2018.01); *G01M 3/202* (2013.01); *G01N 27/304* (2013.01); *G01N 27/404* (2013.01); *G01N 27/4074* (2013.01)

(58) Field of Classification Search
CPC .. F24F 11/36; F24F 11/70; F24F 11/30; F24F 2110/50; F24F 2110/66; G01N 27/4075; G01N 27/304; G01N 27/4074; G01N 27/404; G01M 3/228; G01M 3/202; Y02A 50/249; Y02B 30/78
See application file for complete search history.

(56) References Cited

U.S. PATENT DOCUMENTS

| | | | |
|---|---|---|---|
| 4,637,987 A | 1/1987 | Minten et al. | |
| 4,890,459 A | 1/1990 | Havemann | |
| 5,173,166 A * | 12/1992 | Tomantschger ... | G01N 27/4045 204/412 |

(Continued)

FOREIGN PATENT DOCUMENTS

| | | |
|---|---|---|
| EP | 0075835 A2 | 4/1983 |
| EP | 1921123 A1 | 5/2008 |

(Continued)

*Primary Examiner* — J. Christopher Ball
(74) *Attorney, Agent, or Firm* — Cantor Colburn LLP

(57) ABSTRACT

An HVAC system is provided having an air supply system, a refrigerant circuit configured to condition air in the air supply system, and an electrochemical sensor configured to detect a refrigerant leak from the refrigerant circuit.

8 Claims, 6 Drawing Sheets

(56) References Cited

U.S. PATENT DOCUMENTS

| | | | |
|---|---|---|---|
| 5,284,569 | A | 2/1994 | Lee et al. |
| 5,302,274 | A * | 4/1994 | Tomantschger ... G01N 27/4045 204/412 |
| 6,471,136 | B1 | 10/2002 | Chatterjee et al. |
| 6,534,319 | B1 | 3/2003 | Liu |
| 6,610,367 | B2 | 8/2003 | Lewis et al. |
| 6,644,047 | B2 | 11/2003 | Taira et al. |
| 7,224,285 | B2 | 5/2007 | Tiwet et al. |
| 7,779,668 | B2 | 8/2010 | Leck et al. |
| 7,918,977 | B2 | 4/2011 | Dorisio Deininger et al. |
| 8,350,582 | B2 | 1/2013 | Sasaki et al. |
| 8,683,845 | B2 | 4/2014 | Fleischer et al. |
| 2009/0107157 | A1 | 4/2009 | Dube |

FOREIGN PATENT DOCUMENTS

| | | |
|---|---|---|
| JP | H10300294 A | 11/1998 |
| WO | 2014127482 A1 | 8/2014 |

\* cited by examiner

LEAK DETECTION UNIT FOR REFRIGERANT SYSTEM

CROSS-REFERENCE TO RELATED APPLICATION

This application claims the benefit of U.S. provisional patent application Ser. No. 62/093,152, filed Dec. 17, 2014, the entire contents of which are incorporated herein by reference.

FIELD OF THE INVENTION

The subject matter disclosed herein relates to refrigerant systems and, more specifically, to leak detection systems for refrigerant systems.

BACKGROUND OF THE INVENTION

Gas sensors for detecting hydrocarbons or substituted hydrocarbons have been used in various industrial or laboratory settings for process control. As the compounds can also be flammable or explosive, gas detection sensors have also been used for leak detection where such compounds are used or manufactured. Various types of sensors have been used or proposed. Examples include metal oxide semiconductor (MOS) sensors, non-dispersive infrared detector (NDIR) sensors, pellistor (pelletized resistor) sensors, and mixed potential utilizing high-temperature solid electrolytes made of ceramic such as perovskite.

New applications for hydrocarbons or substituted hydrocarbons have created and continue to create new challenges for gas detection sensors. One such application is in the field of cooling and heating, where older chlorinated hydrocarbons (CFCs) were eliminated due to their adverse impact on the earth's ozone layer. Chlorinated fluorocarbons were initially replaced with chlorofluorocarbons R12 (dichlorodifluoroethane); however, continued concerns with their ozone depleting potential (ODP) and new concerns with the compounds' global warming potential (GWP) led to their replacement with fluorinated hydrocarbons like R32. Continued concerns with ODP and GWP, coupled with performance requirements in vapor compression heat transfer systems, have led to the development of new refrigerants such as fluorinated unsaturated hydrocarbons (i.e., fluorinated olefins) like trans-1,333-tetrafluoropropene (R1234ze). However, since refrigerant flow loops in many HVAC and refrigeration systems are at least partially located in interior building spaces, concerns with toxicity and/or flammability risks arising from leaks have created an expanded need for effective gas detection for such compounds. Leak detection and effective flammability control are necessary to ensure safe operation of the next generation of cooling and refrigeration products.

The above types of sensors have been used with varying degrees of success in the industrial or laboratory settings where they have been employed. However, many such sensors have limitations that can impact their effectiveness in demanding new and existing applications. For example, MOS and pellistor sensors are prone to either false alarms due to cross-sensitivity or catalyst poisoning, respectively. Additionally, durability of MOS sensors for detection of fluorinated hydrocarbons is questionable, as HF could be generated that could potentially damage the sensors. NDIR sensors have been used for demand based ventilation, but may be challenging to meet the cost requirement of the residential HVAC market. As implied by the name, high temperature solid electrolyte systems require high temperatures (typically in excess of 500° C.) that render them impractical for many applications such as residential and commercial HVAC and refrigeration systems in terms of cost and lifetime constraints.

In view of the demanding requirements for hydrocarbon gas sensor, there remains a need for new alternatives that may be more appropriate for or function better in certain environments, offer better cost, or enable beneficial modifications to the overall sensor design.

BRIEF DESCRIPTION OF THE INVENTION

In one aspect, an HVAC system is provided having an air supply system, a refrigerant circuit configured to condition air in the air supply system, and an electrochemical sensor configured to detect a refrigerant leak from the refrigerant circuit.

In addition to one or more of the features describe above, or as an alternative, further embodiments may include wherein the sensor is disposed in the air supply system downstream of an evaporator of the refrigerant circuit; a second sensor disposed in the air supply system upstream of the evaporator; a controller in signal communication with the sensor and a blower and a damper of the air supply system, wherein the controller is programmed to: vent air from the air supply system if the sensor detects the refrigerant leak and/or supply outside air to the air supply system if the sensor detects the refrigerant leak; wherein the sensor is a solid polymer electrolyte (SPE) electrochemical (EC) sensor; wherein the sensor is configured to sense hydrocarbons or substituted hydrocarbons, the sensor comprising a housing, a membrane electrode assembly disposed in the housing, the membrane electrode assembly comprising a sensing electrode comprising a first catalyst comprising noble metal nanoparticles, a counter electrode comprising a second catalyst comprising noble metal nanoparticles, and a solid polymer electrolyte disposed between the sensing electrode and the counter electrode, wherein the nanoparticles of the first catalyst are unsupported or are supported on a support other than carbon black, a first current collector in electrical contact with the sensing electrode, a second current collector in electrical contact with the counter electrode, the housing including an opening in fluid communication with the sensing electrode for gaseous refrigerant to contact the sensing electrode, and an electrical circuit connecting the sensing electrode and the counter electrode; wherein first current collector, the second current collector, or each of the first current collector and the second current collector also functions as a gas diffusion medium, and wherein the first current collector, the second current collector, or each of the first current collector and the second current collector is configured as a mesh or felt; wherein the electrical circuit connecting the sensing electrode and the counter electrode include the controller, the controller configured to apply a positive bias voltage to the sensing electrode relative to the counter electrode or a reference electrode, and to measure voltage or current in the electrical circuit connecting the sensing electrode and the counter electrode to detect an electrochemical response from oxidation of hydrocarbons or substituted hydrocarbons at the sensing electrode; and/or wherein the concentrations of hydrocarbons or substituted hydrocarbons are determined according to the electrical signal generated by the sensor.

In another aspect, a method of detecting a refrigerant leak in an HVAC system having an air supply system and a refrigerant circuit configured to condition air in the air supply system is provided. The method includes providing a sensor configured to detect refrigerant from the refrigerant circuit that is present in the air in the air supply system, applying a positive bias voltage to the sensor, conditioning the sensor to establish a baseline response, and measuring voltage or current in the sensor to determine if a refrigerant concentration of the air in the air supply system is greater than a predetermined concentration.

In addition to one or more of the features describe above, or as an alternative, further embodiments may include determining refrigerant concentration according to a predetermined database mapping refrigerant concentration to a sensor temperature and an environmental dew point, and measuring a sensor output change rate to determine whether a refrigerant leak is present; wherein said applying a positive bias voltage comprises applying a positive bias voltage to a sensing electrode relative to a counter electrode or a reference electrode, and wherein said measuring voltage or current comprises measuring voltage or current in an electrical circuit connecting the sensing electrode and the counter electrode to detect an electrochemical response from oxidation of hydrocarbons or substituted hydrocarbons at the sensing electrode; reducing the refrigerant concentration of the air in the air supply system, if the determined refrigerant concentration is greater than the predetermined concentration, by at least one of: venting air from the air supply system and supplying outside air to the air supply system; wherein air is vented from the air supply system, and wherein said venting air comprises moving a damper of the air supply system to a vent position and activating a blower of the air supply system to force air from the air supply system; subsequent to said reducing the refrigerant concentration, measuring voltage or current in the sensor to determine if a refrigerant concentration of the air in the air supply system is greater than a second predetermined concentration, where the second predetermined concentration is less than the predetermined concentration; measuring voltage or current in the sensor to determine if a refrigerant concentration of the air in the air supply system is less than a second predetermined concentration, where the second predetermined concentration is less than the first predetermined concentration, determining if a sensor output variation rate of the sensor is less than a predetermined variation rate or within a predetermined range of variation rates, and updating the sensor baseline if the determined sensor output variation rate is less than the predetermined variation rate or within the predetermined range of variation rates; measuring voltage or current in the sensor to determine if a sensor output variation rate exceeds a predetermined rate, determining whether the sensor output increases more rapidly than a predetermined increase value, and performing a mitigation action including starting a blower and setting a damper to a venting position, to reduce the accumulation of refrigerant in the HVAC system; measuring voltage or current in the sensor when the blower is activated to determine if the refrigerant concentration decreases, measuring voltage or current in the sensor when the blower is activated to determine if the sensor output increase rate is diminishing, determining a fault based on whether the concentration of refrigerant continues to exceed a predetermined value or the sensor output increases after performing the mitigation action, and issuing an audible alarm and sending fault information if the fault is detected.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION OF THE INVENTION

Figure 1:
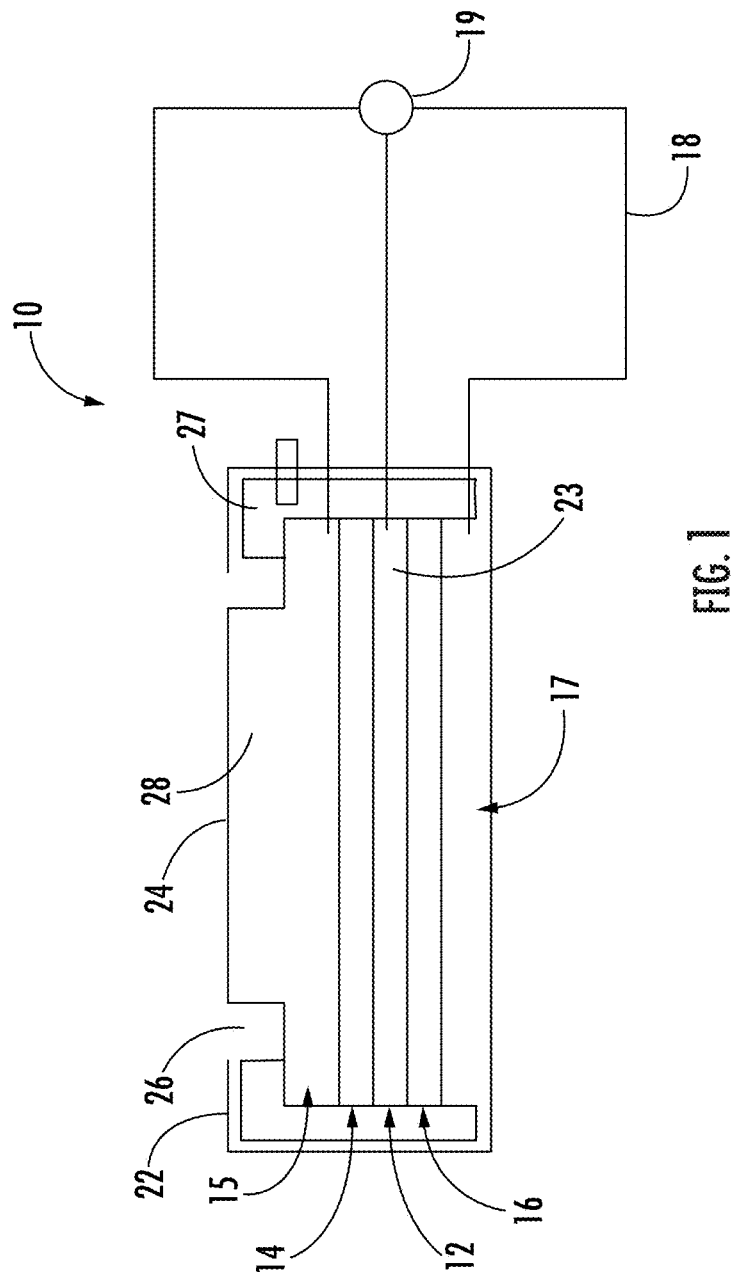
FIG. 1 depicts a simplified schematic representation of a gas sensor as described herein.
Figure 2:
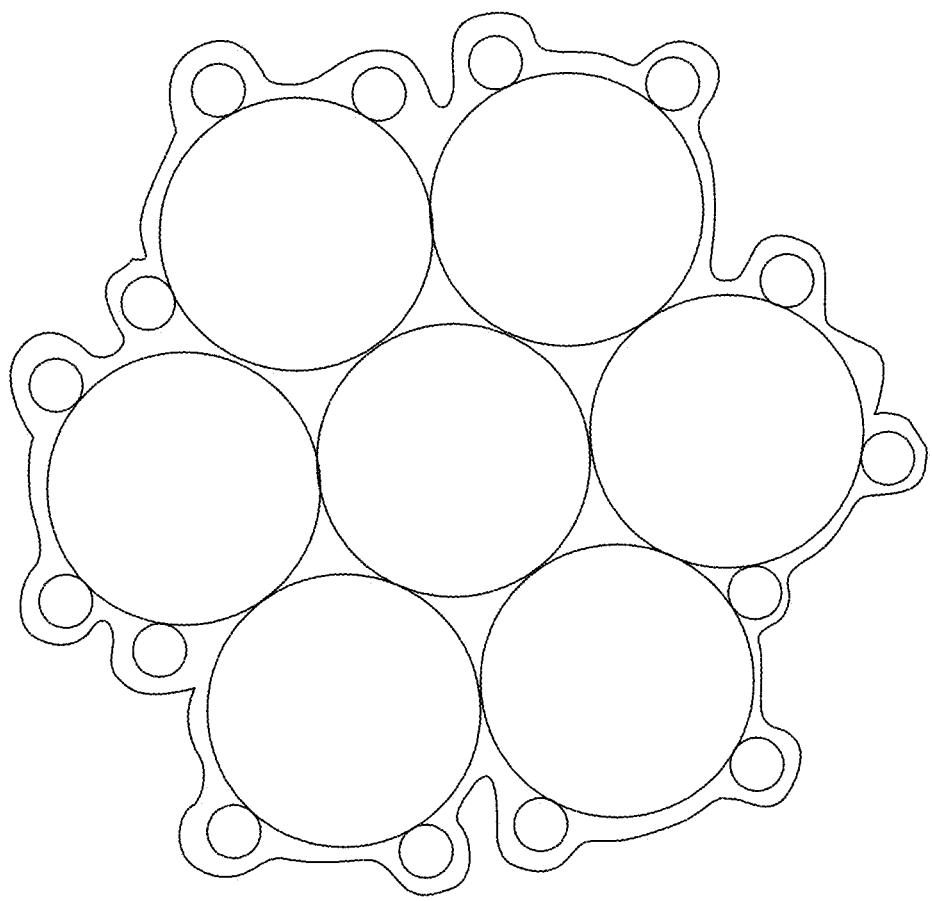
FIG. 2 depicts an exemplary illustration of nanoparticle catalyst supported on a catalyst support along with ion conducting medium such as an ionomer.

An electrochemical (EC) sensor generates quantifiable electrical signals by electrochemically oxidizing or reducing target species present in the environment. In particular, a species in the gaseous phase can be readily detected by an EC sensor if the species has electrochemical activity. A sensor such as an EC sensor 10 is schematically shown in FIG. 1, in which a membrane electrode assembly (MEA) has a solid polymer electrolyte (SPE) (i.e., ion conducting polymer) 12 disposed between sensing electrode 14 and counter electrode 16. Current collectors 15 and 17 are attached to the electrodes and are connected to circuit 18, which includes measurement and/or control device 19. In some embodiments, an optional reference electrode 23 can be disposed in the SPE 12 at a location physically and electrically isolated from the sensing electrode 14 and the counter electrode 16. The current collectors 15, 17 can be formed from a conductive mesh or felt, and are depicted with thickness so that they can also function as gas diffusion media for test gas and reference gas to reach the surface of the electrodes 14, 16. In other embodiments, the current collectors 15, 17 can be relatively thin, almost 2-dimensional conductive screens on the surface of the electrodes 14, 16 with adjacent gas diffusion media that does not have to be conductive. The current collector/gas diffusion medium 15 associated with the sensing electrode 14 can be formed from an oxidation-resistant material such as graphitized carbon or stainless steels. The current collector/gas diffusion medium 17 can be formed from a conductive material such as carbon. Measurement and/or control device 19 can be a voltmeter or ampere meter, but in many cases comprises a potential regulating circuit, microprocessor, or similar electronic device with integrated voltage and or amperage measurement functions and also can apply a constant or variable voltage bias between the sensing electrode 14 and counter electrode 16 during operation of the sensor.

A housing 22 is disposed around the MEA, having an opening 24 to allow a test gas to enter the sensor with the flux of gas regulated by the size of the opening. The opening is shown as completely open, although it is understood that they may be covered with a screen or gas permeable membrane or an adsorber. Also, opening 24 is shown for purposes of illustration as leading directly into chamber 28 for the test gas, but the gas may also be introduced into interior chambers through channel(s) that lead from an outer surface of the sensor to interior chambers. The edges of the electrode assembly membrane can be sealed against seal 27 formed of a seal material such as rubber so that the test gas is kept on the sensing electrode side of the MEA, although other techniques known in the art (e.g., disposing the MEA in a frame (not shown) that is sealed to the edges of the housing) can be used. Though the seal prevents the test gas from entering the counter electrode side, it was found that even with passage of the test gas into the counter electrode side, the sensor can still function properly to determine the presence of hydrocarbons or substituted hydrocarbons. Accordingly, the counter electrode 16 can also be exposed to the test gas from a passage (not shown) leading from opening 24 or from another opening in the housing 22. The electrodes 14, 16 can be bonded to the solid polymer electrolyte as depicted in FIG. 1, but can also be held together by other means such as mechanical clamping force without compromising the functionalities of the sensor.

Of course, the embodiment depicted in FIG. 1 is schematic and exemplary in nature, and other configurations can be used as well. Exemplary gas sensor configurations and variations thereon are disclosed, for example, in U.S. Pat. Nos. 5,650,054, 5,573,648, 6,200,443, 6,948,352, US 2009/0184005 A1, and US 2010/0012494 A1, the disclosures of which are incorporated herein by reference in their entirety.

The precise composition of the electrodes, and materials used in fabricating them, will depend on the particular hydrocarbons being tested for and on design parameters for the sensor and other system components with which it is used. A variety of catalytic noble metals and their alloys (e.g., iridium, rhenium, palladium, platinum, copper, indium, rubidium, silver, gold) can be used to form the electrodes. In some exemplary embodiments, the sensing and/or counter electrodes comprise platinum or a binary or ternary platinum alloys such as PtNi, PtFe, PtCo, PtRu, PtRuNi, PtCr, PtCoCr, PtIrCo, or PtCuFe, wherein the Pt content in atomic ratio ranges from 20% to 100%. In some palladium, or a mixture or alloy of platinum and palladium. In some exemplary embodiments, the sensing and/or counter electrodes comprise palladium or a palladium alloy such as PdAg, PdNi, PdCu, PdRu, or PdY. The counter electrode can comprise a catalyst comprising noble metal that is different from the sensing electrode catalyst metal(s). The catalysts in the counter electrode can be chosen to facilitate oxygen reduction reaction. Electrodes used in electrochemical sensors typically include an electrically conductive material in addition to the noble metal catalyst, and this is often provided by disposing nanoparticles of noble metal catalyst on larger particles of conductors such as carbon black, which is commonly referred to as a carbon-supported catalyst. However, for the detection of hydrocarbons involving oxidation of the hydrocarbons on the sensing electrode, the electrode potentials needed to effectively oxidize hydrocarbons such as olefins and substituted olefins (e.g., fluorinated olefins) exceed the thermodynamic oxidation of carbon support materials, (e.g., 207 mV vs. standard hydrogen electrode). Accordingly, the sensing electrode of the sensors described herein can comprise unsupported (neat) catalysts or catalysts supported on an oxidation-resistant support that is different from carbon black. In the case of a supported catalyst for the sensing electrode, the catalyst is supported on an oxidation-resistant conductive support, which can comprise oxidation-resistant support particles that are typically larger than the catalyst nanoparticles. By "oxidation-resistant, it is meant that at the operational positive voltage bias of the sensor (i.e., 100 to 400 mV), the material of the support particles produces a baseline signal that drifts less than $\frac{1}{5}^{th}$ of the signal generated by a test gas or refrigerant such as R1234ze. A stable baseline may exhibit a drift rate less than 0.48 µA/cm2/yr, or 0.011 µA/cm2/1000 h. Examples of materials for the oxidation-resistant support in the sensing electrode include, but are not limited to graphitized carbon, carbon nanotubes (CNT), and conductive or semi-conductive metal oxides such as $TiO_2$, $WO_3$, $SnO_2$, etc.

The sensor can be operated by applying a positive bias voltage to the sensing electrode relative to the counter electrode or a reference electrode, exposing the sensing electrode to the gas being tested, measuring voltage or current in an electrical circuit connecting the sensing electrode and the counter electrode, and converting the measured voltage or current to a reading indicative of the presence and/or concentration of the component in the gas being tested. Oxidation of hydrocarbons or substituted hydrocarbons at the sensing electrode will cause an electrochemical response that can be detected as voltage or current in the circuit. In some embodiments, the potential regulating circuit, microprocessor, or similar device 19 is configured to apply the positive voltage bias and measure the response voltage or current. In some embodiments, the positive voltage bias applied to the sensing electrode relative to the counter electrode is from 20 mV to 800 mV. In some embodiments, the applied positive voltage bias can be applied as a constant positive voltage bias ranging from 200 mV to 400 mV. In some embodiments, the positive voltage bias can be varied within the 20 mV to 800 mV range by an amount of up to 400 mV.

The sensor can detect various hydrocarbons such as ethane, propane, and substituted hydrocarbons such as fluorinated hydrocarbons (e.g., difluoromethane or R32, 1,1-difluoroethane or R152a, 1,1,1,2-tetrafluoroethane or R134a) or chlorinated hydrocarbons (e.g., chloromethane or R40). Olefins, including fluoro-substituted olefins that offer low-ODP and low-GWP potential as well as good performance as refrigerants, can be difficult to detect using prior art sensors. In some embodiments, the sensors described herein are used to detect olefins such as propene. In some embodiments, the sensors described herein are used to detect substituted olefins such as fluoro-substituted olefins, e.g., any of the isomers of tetrafluoropropene (e.g., R1234ze, R1234yf, R1234zd).

Figure 5:
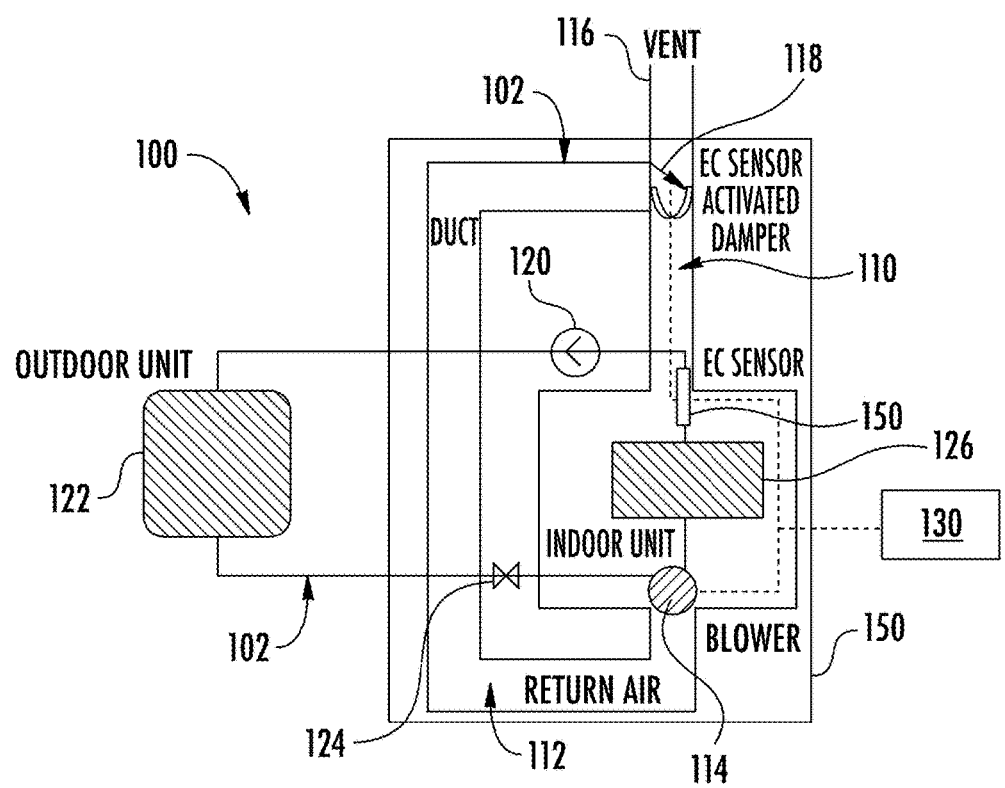
FIG. 5 is a schematic view of an exemplary residential split cooling system that may utilize the sensor shown in FIG. 1.

Expected replacement of current generation of high GWP refrigerants with mildly flammable low GWP refrigerants will require the ability to detect refrigerant leak and to mitigate and/or eliminate the potential flammability. EC sensors are a cost effective sensor for detecting toxic gases such as carbon monoxide, hydrogen sulfide, etc. However, some conventional EC sensors have neither sufficient activity towards the low GWP refrigerant, nor the long lifetime and reliability demanded by residential and commercial HVAC systems. Consequently, the use of EC sensor 10 with a specific design and material selection requires different protocols to enable the sensor functionalities to direct system level mitigation if a refrigerant leak occurs. One exemplary system scheme is illustrated in FIG. 5, which depicts EC sensor 10 regulating a blower or fan 114, and a damper 118 when a refrigerant leak is detected and the concentration of flammable refrigerant(s) exceeds a threshold value pre-set by the system. System mitigation response to suppress the flammability of the refrigerant/air mixture resulting from the leak includes increasing air flow to dilute the refrigerant released into a circulation duct, and circulating the refrigerant containing air to the outdoor environment by opening a damper that allows air to be ultimately discharged to the ambient. The low GWP refrigerant EC sensor 10 exhibits unique characteristics that require a specifically designed control protocol to ensure reliable responsiveness and effective system risk mitigation capability in the event of a refrigerant leak. Specific operation logic of sensor 10 may include initiation, sensor baseline compensation and correction, refrigerant flammability quantification, component state based fault detection, and event driven or periodic sensor regeneration.

The invention is further described in the following examples.

EXAMPLES

Figure 3:
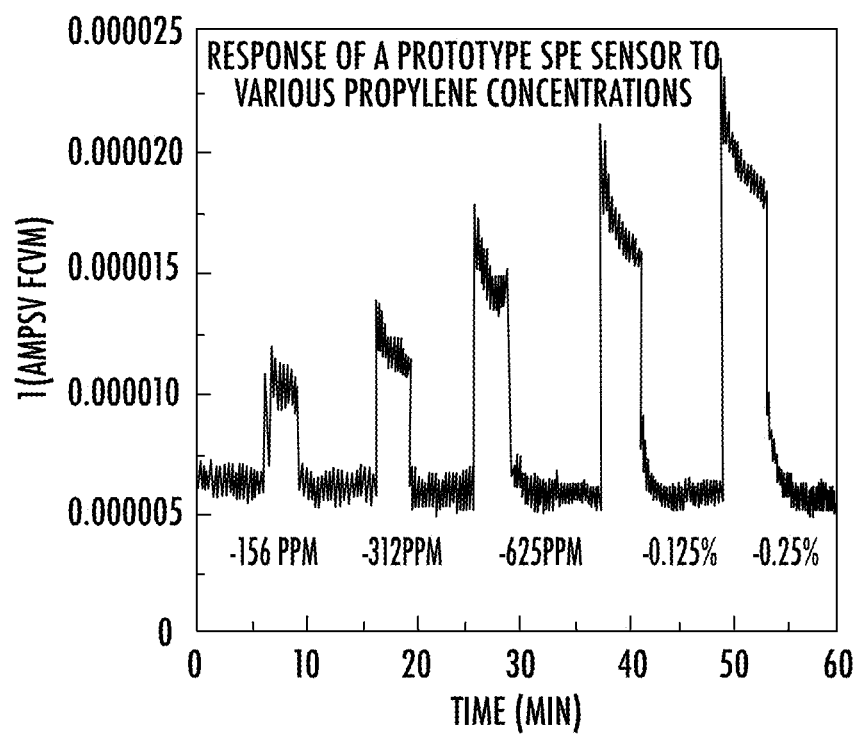
FIG. 3 depicts output of a sensor as described herein in response to exposure to propylene.
Figure 4:
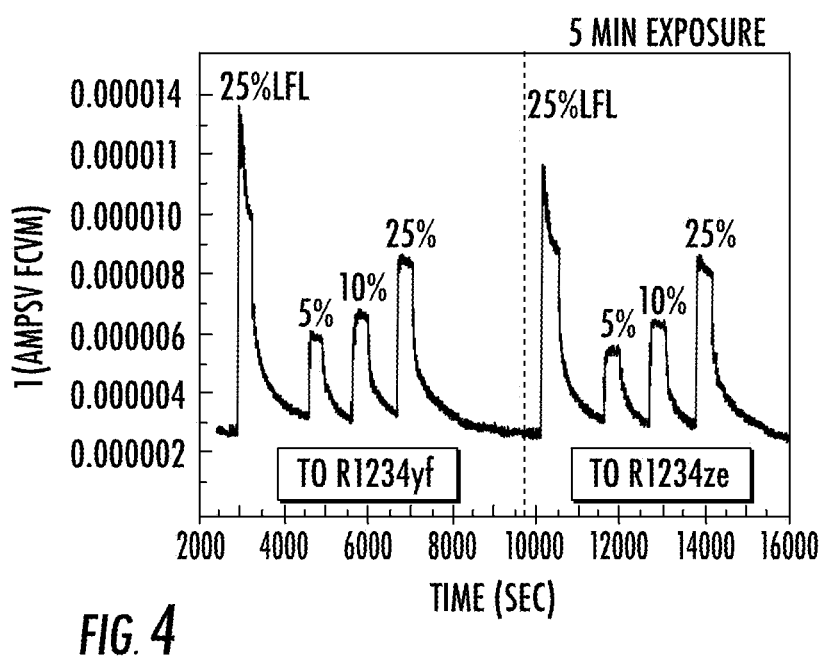
FIG. 4 depicts output of a sensor as described herein in response to exposure to 2,333-tetrafluoropropene (R1234yf) and trans-1,333-tetrafluoropropene (R1234ze) respectively.

A prototype sensor configured as shown in FIG. 1 without a reference electrode was operated with a positive voltage bias of 300 mV at the sensing electrode relative to the counter electrode and exposed to air, which was mixed periodically with varying concentrations of propylene. The sensor response is shown in FIG. 3. As shown in FIG. 3, the sensor effectively identified propene with a response that increased with increasing to propene concentration. In a separate test, the air was mixed periodically with varying concentrations of R234yf or R1234ze. The sensor response is shown in FIG. 4, which shows that the sensor effectively identified the compounds with a response that increased with increasing concentration.

FIG. 5 illustrates an exemplary refrigeration or HVAC system 100 that generally includes an air supply system 102, a refrigerant circuit 104, and a gas sensor 106 (e.g., gas sensor 10).

Air supply system 102 includes an air supply duct 110, a return air duct 112, a blower 114, an air vent 116, and a damper 118. Air supply duct 110 supplies air conditioned by refrigerant circuit 104 to a serviced space 150 such as, for example, a house or office building. Return air duct 112 supplies air from the space to be conditioned to heat exchange unit evaporator coils 126, and blower 114 circulates the air conditioned by coils 126 into air supply duct 110. Damper 118 is movable between an open position and a closed position to selectively vent air from system 102 or to allow outside air into system 102.

Refrigerant circuit 104 generally includes a compressor 120, a condenser 122, an expansion device 124, and an evaporator 126. Refrigerant circuit 104 functions in a manner well known in the art.

In the exemplary embodiment, gas sensor 106 is a solid polymer electrolyte (SPE) electrochemical (EC) sensor that is disposed within air supply system 102 downstream of evaporator 126 to detect a refrigerant leakage in refrigerant circuit 104. One or more additional sensors 106 may be disposed throughout air supply system 102 such as, for example, upstream of evaporator 126 in return air duct 112.

As described herein, sensor 106 produces a voltage or current signal in the presence of predetermined types of refrigerants (e.g., flammable, low GWP refrigerants). In the exemplary embodiment, sensor 106 is constructed with a precious metal catalyst coated ion conducting membrane, gas diffusion media, and current collectors. Electrochemical oxidation of predetermined gas constituents (e.g., refrigerants, hydrofluoroolefins), which is facilitated by catalysts, produces measureable current signal, which is sent to a controller 130.

In the exemplary embodiment, controller 130 is in signal communication with sensor 106, blower 114, and damper 118. When a refrigerant leak occurs within system 100, gas sensor 106 sends a signal indicative of such to controller 130. The current or voltage of the signal varies depending on the concentration of the refrigerant. For example, a higher concentration of the refrigerant causes gas sensor 106 to produce a higher current signal. Controller 130 receives the current signal, and depending on the determined refrigerant concentration, performs a desired mitigation action. In the exemplary embodiment, the mitigation actions include operating blower 114 and damper 118 to either add air to the system (dilution) or vent the contaminated air out of the system (e.g., via air vent 116), activate a warning or alarm system (issue audible, visual, wireless, etc. warnings), and/or shutting down one or more components of HVAC system 100.

Figure 6:
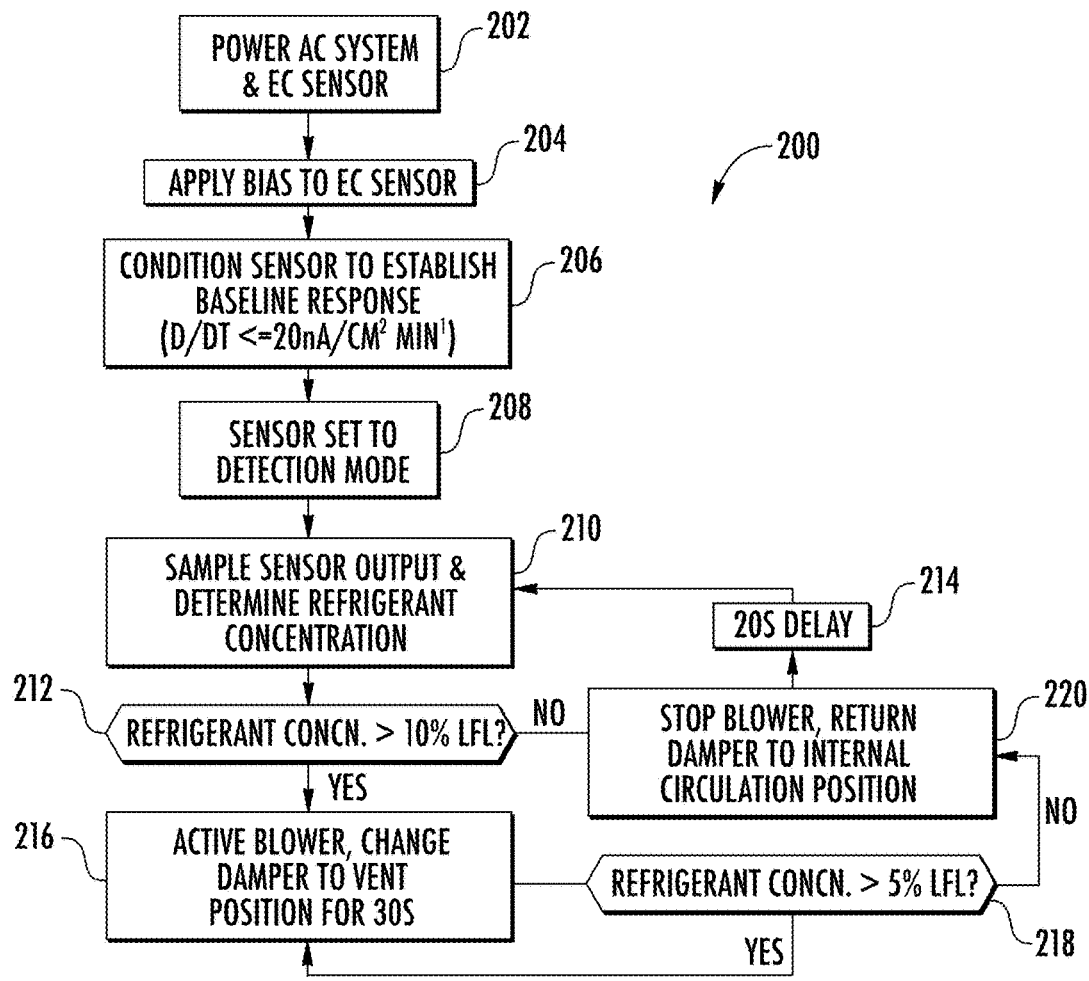
FIG. 6 is a schematic view of an exemplary control diagram of the cooling system shown in FIG. 5 that includes the initialization of an electrochemical sensor following installation or replacement.

FIG. 6 illustrates an exemplary control operation 200 for HVAC system 100 such as during sensor initiation for a new installation or re-initiation following operation interruption (e.g., a power outage). Control 200 includes powering refrigerant circuit 104 and gas sensor 106 at step 202. At step 204, a positive bias voltage is applied to gas sensor 106. At step 206, gas sensor 106 is conditioned to establish a baseline response (e.g., $di/dt <= \pm 10$ $nA/cm^2$ $min^{-1}$ taking into account sensor baseline dependence on environment humidity and temperature changes).

One exemplary method to determine baseline value includes continually sampling the sensor current output and running a moving average calculation of the output for a predetermined period (e.g., 3 to 30 seconds). The baseline response is then corrected based on the humidity and temperature variation during which the baseline current is registered. Corrected baseline response during a predetermined period (e.g., 15-120 minutes) is stored in the internal memory for determining the drift rate. The baseline response in clean air can vary as a result of system reset, for example after a power outage, in addition to environmental humidity variation. The corrected baseline drift generally decreases over time for continuous operation, providing the basis to determine the presence of refrigerants or other contaminants when the sensor response change rate substantially exceeds the typical or predetermined drift rate (e.g. $\pm 10$ $nA/cm^2$ $min^{-1}$)

At step 208, sensor 106 is set to a detection mode where sensor 106 is operable to detect a refrigerant leakage in refrigerant circuit 104. Though the example above may assume the sensor is set to detection mode only after stable sensor baseline is established, the sensor can still perform its detection functionalities during the stabilization phase to sense refrigerant leak based on the sensor response change rates. This dual mode operation is based on the downward trending characteristics of baseline (negative rate) during sensor stabilization, which is altered or reversed upon electrochemical reactions of gaseous species present. A parallel logic function may be incorporated in the sensor or controller firmware to enable the dual operation modes.

At step 210, controller 130 receives the output current from sensor 106 and determines the refrigerant concentration based on a predetermined relationship between a specific refrigerant concentration and sensor output current density (normalized with respect to the apparent area of the electrode in the EC sensor). Determination of a refrigerant leak may be based on either sensor output change rate or whether the steady output differs significantly from the baseline current. Specifically, when the current registered by a sensor increases at a rate exceeding a predetermined rate (e.g., 0.02 µA/cm², or 0.1 µA/cm²), a refrigerant leak or other contaminants may be present, which would trigger system action.

Figure 7:
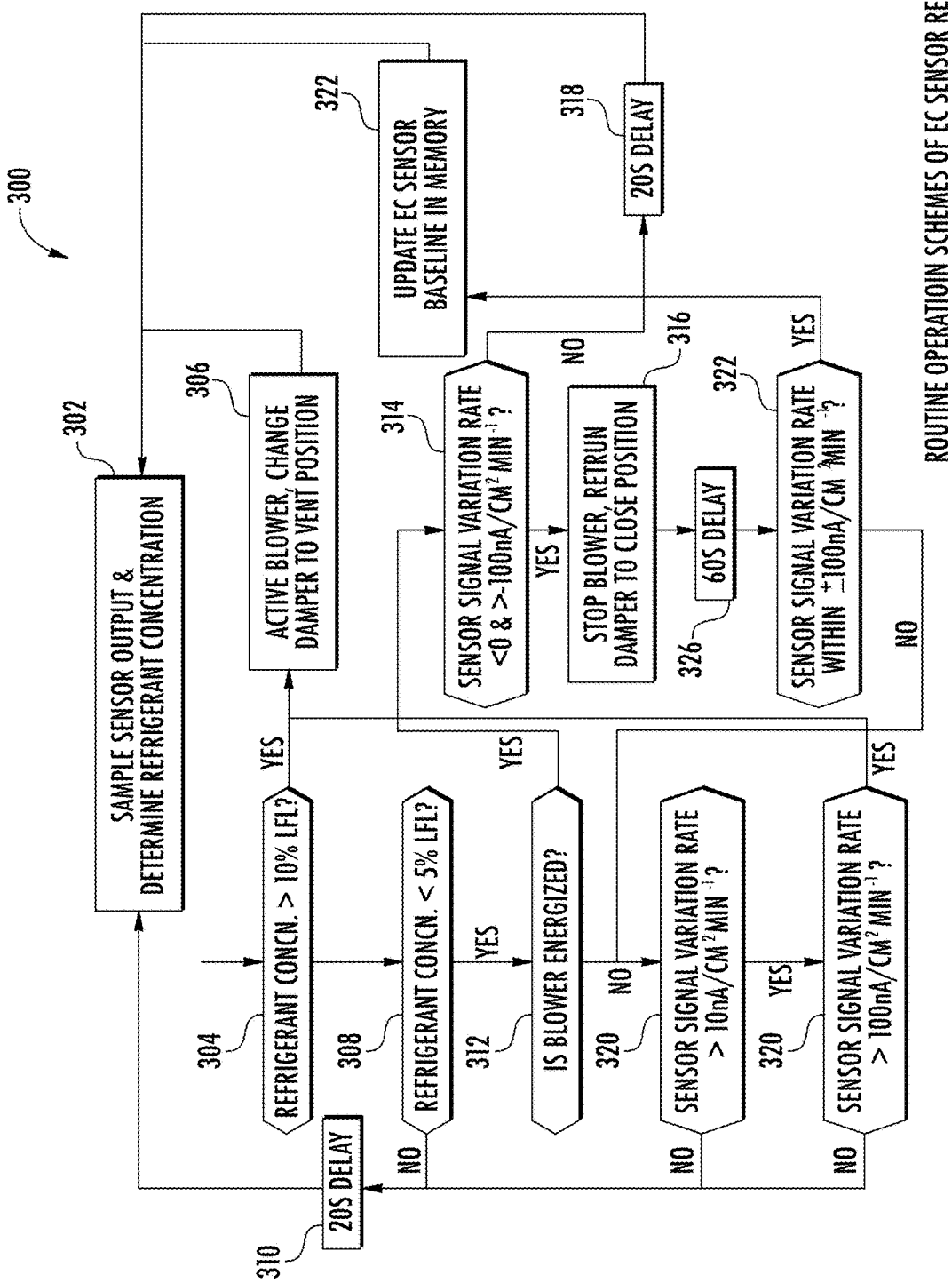
FIG. 7 is a schematic view of another exemplary control diagram of the HVAC system shown in FIG. 5 during an exemplary routine operation.

In some situations where the mitigation step of air circulation is not sufficient to mitigate the accumulation of refrigerant/contaminant, the sensor output can continue to rise to plateau at a value substantially higher than the baseline sensor output. At this point, the net sensor output is calculated by subtracting baseline current to determine the concentration of the refrigerant or contaminant present or an equivalent concentration, based on which enhanced system mitigation can be taken to mitigate the accumulated refrigerant/contaminant until either the net sensor output indicates less than a predetermined concentration (e.g., less than 5% LFL concentration) or the sensor reading remains stable within a predetermined range (e.g., ±10 nA/cm² min$^{-1}$). The sensor output stability may be used to determine whether baseline current needs to be updated as well, as shown in the example of FIG. 7. If enhanced mitigation action has been taken, but sensor output remains above an allowed value (e.g., 25% LFL equivalent), system fault information may be registered and elevated action may be taken such as an audible alarm and/or a reminder for maintenance. Before the fault is determined, a series of component state checks may be performed as described herein (see FIG. 7), where both blower state and damper position are determined along with the flammability level as indicated by the sensor.

Accuracy of refrigerant concentration determination may be further improved by accounting for the environmental dew point according to an empirical relationship or mapping the sensitivity to the dew point for a given sensor operating temperature. The dependence of sensitivity on temperature and dew point may be illustrated by the equation $i_s$(µA/cm²/ppm)=$f(T, T_{d.p})$, where $i_s$ is the sensitivity towards a specific refrigerant where sensor current density output is normalized with respect to refrigerant concentration (ppm: parts per million), T is the sensing element temperature that can be the same or different from the ambient temperature if active temperature control is incorporated, and $T_{d.p}$ is the dew point of the environment that indicates water vapor content.

With the sensitivity mapped to sensor temperature and environmental dew point, the refrigerant concentration may then be determined according to $$c_{ref}(\text{ppm}) = \frac{i_o}{i_s},$$

where $i_o$ is the net sensor output current density derived by subtracting the baseline current density from actual sensor reading when the refrigerant leak is determined. The refrigerant concentration can be readily converted to LFL which is further transformed to executable commands to the controller. As an example, the LFL of R1234ze is 70000 ppm.

At step 212, controller 130 determines whether the refrigerant concentration is greater than a first predetermined concentration (e.g., 10% LFL). If the concentration is not greater than the first predetermined concentration, the operation returns to step 210 via an optional delay (step 214). If the concentration is greater than the first predetermined concentration, at step 216, controller 130 performs a leak mitigation action such as moving damper 118 to a vent position (e.g., open position, which may be performed with or without an active actuation mechanism) and activating or operating blower 114 for a predetermined amount of time (e.g., 30 seconds). As described herein, the system mitigation action may be elevated or terminated based on how effective the mitigation or reversal of refrigerant/contaminant accumulation is according to either sensor output change rate or the steady sensor output differing from the baseline current.

At step 218, controller 130 determines if the refrigerant concentration is greater than a second predetermined concentration (e.g., 5%) that is less than the first predetermined concentration. If the refrigerant concentration is greater than the second predetermined concentration, the operation returns step 216 to continue the system mitigation action. If the refrigerant concentration is not greater than the second predetermined concentration, at step 220, controller 130 stops operation of blower 114 and returns damper 118 to an internal circulation position. The operation may then return to step 210 via optional delay (step 214). As such, step 210 determines whether a refrigerant leak or contaminants may be present according to either sensor output change rate or the steady sensor output differing from the baseline current. Success and subsequent termination of the mitigation action may be determined based on the absolute refrigerant concentration sensing by sensor(s) 10.

FIG. 7 illustrates an exemplary control operation 300 for HVAC system 100 that includes sensor baseline correction. At step 302, controller 130 receives the output from sensor 106 and determines the refrigerant concentration, as described herein. At step 304, controller 130 determines whether the refrigerant concentration is greater than a first predetermined concentration (e.g., 10% LFL). If the concentration is greater than the predetermined concentration, at step 306, controller 130 performs leak mitigation actions such as moving damper 118 to a vent position (e.g., open position) and activating or operating blower 114 for a predetermined amount of time (e.g., 30 seconds) prior to re-assessing the concentration in step 302.

If the concentration is not greater than the predetermined concentration, at step 308, controller determines if the refrigerant concentration is less than a second predetermined concentration (e.g., 5% LFL) that is less than the first predetermined concentration. If the refrigerant concentration is less than the second predetermined concentration, the operation returns to step 302 via an optional delay (e.g., 20 seconds) at step 310. If the refrigerant concentration is not less than the second predetermined concentration, at step 312, controller 130 determines if blower 114 is energized.

If blower 114 is energized, at step 314, controller 130 determines if the sensor output current decreases with time (<0) but the decreasing rate is less than a predetermined rate (e.g., 10 nA/cm² min$^{-1}$). If sensor output variation is greater than a predetermined variation (e.g., 0 nA/cm² min$^{-1}$, and increasing) step 302 is repeated after a delay at 318. If sensor output evolution is less than a predetermined variation (10 nA/cm² min$^{-1}$ and decreasing), the controller 130 stops operation of blower 114 and returns damper 118 to a closed position, at step 316.

After a predetermined delay (e.g., 60 seconds) at 326, the sensor output rate is subsequently checked again to determine if the baseline variation with within a predetermined variation (e.g., ±10 nA/cm² min$^{-1}$). If the baseline variation rate is within the predetermined variation, a new baseline value is updated in the sensor memory via step 322 before the routine concentration determination is repeated at step 302. If the baseline variation rate is greater than the predetermined variation rate, the method returns to step 320 to determine whether a mitigation action should be taken based on how rapidly sensor output evolves, as described herein in more detail.

If blower 114 is not energized or the baseline variation rate is greater than the predetermined variation, at step 320, controller 130 determines if sensor output is increasing at a rate greater than a predetermined variation rate (e.g., 10 $nA/cm^2$ $min^{-1}$). If the sensor output signal variation rate is not greater than the predetermined variation rate, the operation returns to step 302 via a predetermined delay (step 310). If the sensor output variation rate is greater than the predetermined variation rate, controller 130 further determines if the sensor output increase is rapid enough (e.g., >100 $nA/cm^2$ $min^{-1}$) to indicate the presence of refrigerants or contaminants at step 330, leading to activating mitigation action by performing step 306. If the sensor output increasing rate is less than the predetermine output increase (100 $nA/cm^2$ $min^{-1}$), the method returns to step 302 to determine refrigerant/contaminant concentration based on the absolute sensor output as opposed to the output change rate.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. An HVAC system comprising:
   an air supply system;
   a refrigerant circuit configured to condition air in the air supply system; and
   an electrochemical sensor configured to detect a refrigerant leak from the refrigerant circuit;
   wherein the sensor is a solid polymer electrolyte (SPE) electrochemical (EC) sensor, wherein the sensor is configured to sense hydrocarbons or substituted hydrocarbons, the sensor comprising:
   a housing;
   a membrane electrode assembly disposed in the housing, the membrane electrode assembly comprising a sensing electrode comprising a first catalyst comprising noble metal nanoparticles, a counter electrode comprising a second catalyst comprising noble metal nanoparticles, and a solid polymer electrolyte disposed between the sensing electrode and the counter electrode;
   wherein the nanoparticles of the first catalyst are supported on the support, the support comprising an oxidation-resistant conductive support including oxidation-resistant support particles larger than the nanoparticles of the first catalyst.

2. The system of claim 1, wherein the sensor is disposed in the air supply system downstream of an evaporator of the refrigerant circuit.

3. The system of claim 2, further comprising a second sensor disposed in the air supply system upstream of the evaporator.

4. The system of claim 1, further comprising a controller in signal communication with the sensor and a blower and a damper of the air supply system, wherein the controller is programmed to:
   vent air from the air supply system if the sensor detects the refrigerant leak; and/or
   supply outside air to the air supply system if the sensor detects the refrigerant leak.

5. The system of claim 1 wherein the sensor is configured to sense hydrocarbons or substituted hydrocarbons, the sensor further comprising:
   a first current collector in electrical contact with the sensing electrode;
   a second current collector in electrical contact with the counter electrode;
   the housing including an opening in fluid communication with the sensing electrode for gaseous refrigerant to contact the sensing electrode; and
   an electrical circuit connecting the sensing electrode and the counter electrode.

6. The system of claim 5, wherein first current collector, the second current collector, or each of the first current collector and the second current collector also functions as a gas diffusion medium, and wherein the first current collector, the second current collector, or each of the first current collector and the second current collector is configured as a mesh or felt.

7. The system of claim 5, wherein the electrical circuit connecting the sensing electrode and the counter electrode include the controller, the controller configured to apply a positive bias voltage to the sensing electrode relative to the counter electrode or a reference electrode, and to measure voltage or current in the electrical circuit connecting the sensing electrode and the counter electrode to detect an electrochemical response from oxidation of hydrocarbons or substituted hydrocarbons at the sensing electrode.

8. The system of claim 7, wherein the concentrations of hydrocarbons or substituted hydrocarbons are determined according to the electrical signal generated by the sensor.

* * * * *